(12) United States Patent
Tanaka et al.

(10) Patent No.: US 12,098,303 B2
(45) Date of Patent: Sep. 24, 2024

(54) FIXING MEMBER AND LAMINATED BODY

(71) Applicant: ZEON CORPORATION, Tokyo (JP)

(72) Inventors: Hidekazu Tanaka, Tokyo (JP); Atsushi Sone, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 801 days.

(21) Appl. No.: 17/287,424

(22) PCT Filed: Oct. 31, 2019

(86) PCT No.: PCT/JP2019/042909
§ 371 (c)(1),
(2) Date: Apr. 21, 2021

(87) PCT Pub. No.: WO2020/091005
PCT Pub. Date: May 7, 2020

(65) Prior Publication Data
US 2021/0355352 A1    Nov. 18, 2021

(30) Foreign Application Priority Data

Nov. 2, 2018  (JP) ................................. 2018-207616

(51) Int. Cl.
*C09J 11/08* (2006.01)
*A61B 17/132* (2006.01)
(Continued)

(52) U.S. Cl.
CPC .......... *C09J 11/08* (2013.01); *A61B 17/1322* (2013.01); *B32B 27/308* (2013.01); *C09J 7/38* (2018.01); *C09J 201/00* (2013.01); *A61B 2017/00858* (2013.01); *B32B 7/12* (2013.01); *B32B 2307/538* (2013.01); *B32B 2307/744* (2013.01);
(Continued)

(58) Field of Classification Search
CPC ... C09J 11/08; C09J 7/38; C09J 201/00; C09J 2203/326; C09J 2203/358; C09J 2301/302; C09J 2301/408; C09J 2483/00; C09J 5/00; C09J 2475/00; A61B 17/1322; A61B 2017/00526; A61B 2017/00858; B32B 27/308; B32B 7/12; B32B 2307/538; B32B 2307/744; B32B 2405/00; B32B 2535/00; B32B 7/04
See application file for complete search history.

(56) References Cited

U.S. PATENT DOCUMENTS

2019/0092986 A1    3/2019  Sone

FOREIGN PATENT DOCUMENTS

| JP | 3210060 U | 4/2017 |
| JP | 2018092039 A | 6/2018 |
| WO | 2017188118 A1 | 11/2017 |

OTHER PUBLICATIONS

Dec. 17, 2019, International Search Report issued in the International Patent Application No. PCT/JP2019/042909.
(Continued)

*Primary Examiner* — John D Freeman
(74) *Attorney, Agent, or Firm* — KENJA IP LAW PC

(57) ABSTRACT

Disclosed is a fixing member in which adhesion of foreign substances to its surface is suppressed, and which hardly causes lateral displacement when such fixing members are attached together to form a joined state. The fixing member disclosed herein includes a surface having a coefficient of kinetic friction of 1.50 or less, an arithmetic mean roughness Ra of 5.00 μm or less, and a shear stress at the time of self-attachment of 100.00 N or more.

8 Claims, 6 Drawing Sheets

(51) Int. Cl.
*B32B 7/12* (2006.01)
*B32B 27/30* (2006.01)
*C09J 7/38* (2018.01)
*C09J 201/00* (2006.01)
*A61B 17/00* (2006.01)

(52) U.S. Cl.
CPC ....... *B32B 2405/00* (2013.01); *B32B 2535/00* (2013.01); *C09J 2203/326* (2013.01); *C09J 2203/358* (2020.08); *C09J 2301/302* (2020.08); *C09J 2301/408* (2020.08); *C09J 2483/00* (2013.01)

(56) References Cited

OTHER PUBLICATIONS

Apr. 27, 2021, International Preliminary Report on Patentability issued in the International Patent Application No. PCT/JP2019/042909.

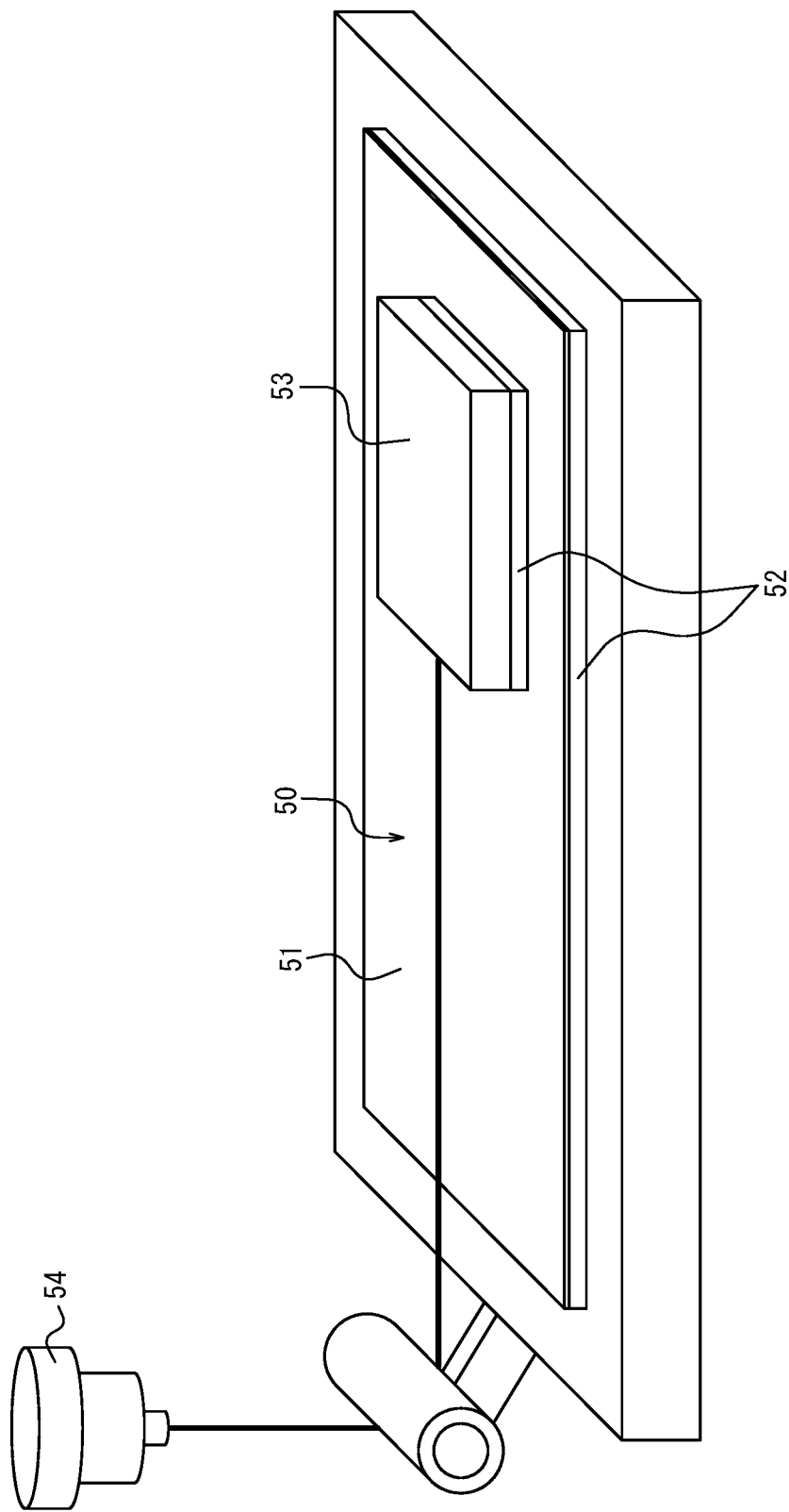

FIXING MEMBER AND LAMINATED BODY

TECHNICAL FIELD

This disclosure relates to a fixing member and a laminated body comprising the same.

BACKGROUND

Conventionally, for example, for the purpose of joining the abutting surfaces of two articles or joining the two different abutting portions of one article, a member capable of bonding the abutting surfaces of the objects to be joined by means of abutment (hereinafter referred to as a "fixing member") is used on the abutting surfaces.

Examples of an article using such a fixing member include tourniquets. A tourniquet has, for example, a rubber substrate and touch fasteners such as hook-and-loop fasteners at the longitudinal ends of the rubber substrate. Then, the tourniquet is wound around the arm to join the touch fasteners at both ends together such that the arm is tightened, and hemostasis is achieved by the tightening pressure.

It has also been proposed that a self-adhesive tape usable as a fixing member be used directly as a tourniquet (see, for example, JP 3210060 U (PTL 1)).

PTL 1 describes a tourniquet made of a self-adhesive tape alone. According to PTL 1, when the self-adhesive tape is wrapped around an object in an overlapping manner, the overlapping parts of the tape substrate can adhere to each other by the self-adhesiveness.

CITATION LIST

Patent Literature

PTL 1 JP 3210060 U

SUMMARY

Technical Problem

In a state in which two fixing members are joined (hereinafter abbreviated as a "joined state"), it is necessary to prevent displacement of the two fixing members in a direction parallel to the joining surfaces (hereinafter referred to as "lateral displacement") and to suppress unintentional separation of the fixing members. However, when the adhesiveness (especially in the direction perpendicular to the joining surfaces) between the fixing members is increased to prevent lateral displacement of the fixing members in a joined state, there is a problem that foreign substances such as paper scraps and specks of lint also tend to adhere to the surfaces of the fixing members before reaching a joined state. The adhesion of such foreign substances may damage the appearance of the fixing members and may even cause lateral displacement of the fixing members.

In other words, there is room for improvement in the above conventional technology in terms of preventing foreign substances from adhering to the surfaces of the fixing members while suppressing separation of the fixing members due to lateral displacement of the fixing members in a joined state.

It would thus be helpful to provide means for advantageously attaining the aforementioned improvements.

Solution to Problem

The present inventors conducted diligent investigation with the aim of solving the problems set forth above. The present inventors discovered that by keeping the coefficient of kinetic friction and the arithmetic mean roughness Ra of the surface of the fixing member below predetermined values, respectively, and by keeping the shear stress generated when two such fixing members are attached together above a predetermined value, the amount of foreign substances adhering to the surface of the fixing member can be reduced, while suppressing separation of the fixing members due to lateral displacement. The present disclosure was completed based on this discovery.

To advantageously address the above issues, it would thus be helpful to provide a fixing member comprising a surface having a coefficient of kinetic friction of 1.50 or less, an arithmetic mean roughness Ra of 5.00 μm or less, and a shear stress during self-attachment of 100.00 N or more. Thus, in the case of a fixing member having a surface with a coefficient of kinetic friction and an arithmetic mean roughness Ra each being not greater than the above-mentioned value and with a shear stress at the time of self-attachment being not less than the above-mentioned value, when such fixing members are attached to each other to form a joined state, separation of the fixing members due to lateral displacement is suppressed and foreign substances are hardly adhered to their surfaces.

As used herein, the "coefficient of kinetic friction of the surface" of the fixing member is a value that is measured as the coefficient of kinetic friction between the fixing member and a piece of carton paper in accordance with JIS K 7125, and that can be specifically measured as described in the EXAMPLES section below.

As used herein, the "arithmetic mean roughness Ra of the surface" of the fixing member is a value that is measured in accordance with JIS B 0601-2001, and that can be specifically measured as described in the EXAMPLES section below.

As used herein, the "shear stress at the time of self-attachment" of the fixing member is a value that is measured for two such fixing members prepared with a predetermined size and attached together, and that can be specifically measured as described in the EXAMPLES section below.

Here, it is preferable that the fixing member disclosed herein is formed from a cured product of a resin composition, the resin composition containing a resin, a curing agent capable of curing the resin, and a silicone-based surface modifier. When the cured product of the resin composition is used as the fixing member, the adhesion of foreign substances to the fixing member can be sufficiently suppressed.

In the fixing member disclosed herein, it is also preferable that a content of the silicone-based surface modifier in the resin composition is 0.05 parts by mass or more and 1.7 parts by mass or less per 100 parts by mass of the resin. When the cured product of the resin composition containing the silicone-based surface modifier in the above-mentioned amount is used as the fixing member, separation of the fixing members due to lateral displacement can be sufficiently prevented, while the adhesion of foreign substances to the fixing member can be further suppressed.

In the fixing member disclosed herein, it is also preferable that the silicone-based surface modifier is a polydimethylsiloxane-based surface modifier. When the cured product of the resin composition containing a polydimethylsiloxane-based surface modifier is used as the fixing member, adhesion of foreign substances to the fixing member can be further suppressed.

It is also preferable that the fixing member disclosed herein has a surface tackiness (a tackiness of the surface) of 1.60 N or less. If the surface tackiness is not greater than this value, the adhesion of foreign substances to the fixing member can be further suppressed.

As used herein, the "tackiness" of the fixing member can be measured as described in the EXAMPLES section below.

To advantageously address the above issues, it would thus be helpful to provide a laminated body comprising: a substrate; and any of the above-described fixing members. In the laminate with any of the above-mentioned fixing members on the substrate, when the fixing members are attached together to form a joined state, separation of the fixing members due to lateral displacement is suppressed and foreign substances are unlikely to adhere to the surfaces of the fixing members.

To advantageously solve the above-mentioned issues, the present disclosure provides a laminated body comprising: a substrate; a first fixing member located on the substrate; and a second fixing member located on the substrate, wherein the first and second fixing members are abuttable against each other, surfaces of the first and second fixing members each have a coefficient of kinetic friction of 1.50 or less, the surfaces of the first and second fixing members each have an arithmetic mean roughness Ra of 5.00 μm or less, and a shear stress generated when the first and second fixing members are attached together is 100.00 N or more. Thus, in the laminated body that comprises two fixing members with a coefficient of kinetic friction and an arithmetic mean roughness Ra each being not greater than the above-mentioned values, and with a shear stress generated when the fixing members are attached together being not less than the above-mentioned value, when the fixing members are attached together to form a joined state, separation of the fixing members due to lateral displacement is suppressed and foreign substances are unlikely to adhere to the surfaces of the fixing members.

As used herein, the "shear stress when the two fixing members (first fixing member and second fixing member) are attached together" is a value that is measured for two such fixing members prepared with a predetermined size and attached together, and that can be specifically measured as described in the EXAMPLES section below.

In addition, the laminated body disclosed herein is usable as, for example, a tourniquet.

Advantageous Effect

According to the present disclosure, it is possible to provide a fixing member in which adhesion of foreign substances to its surface is suppressed, and which hardly causes lateral displacement when such fixing members are attached together to form a joined state.

Further, according to the present disclosure, it is possible to provide a laminated body that comprises a fixing member in which adhesion of foreign substances to its surface is suppressed, and which hardly causes lateral displacement when such fixing members are attached together to form a joined state.

BRIEF DESCRIPTION OF THE DRAWINGS

In the accompanying drawings.

FIG. 5 is a perspective view schematically illustrating an operation to measure the coefficient of kinetic friction of a surface of a fixing member.

DETAILED DESCRIPTION

Figure 1A:
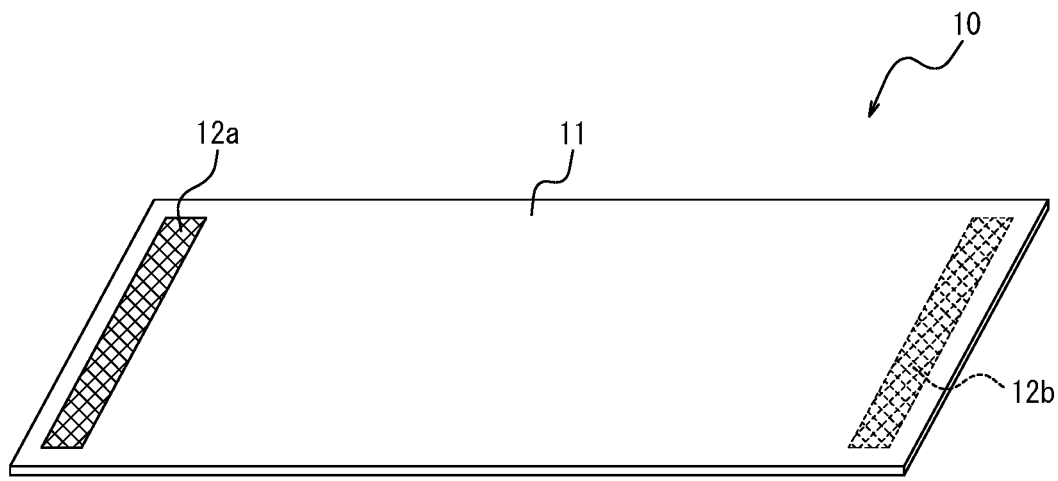
FIG. 1A is a perspective view of a laminated body 10, which is an example of an embodiment of the laminated body according to the present disclosure.

The following describes embodiments of the present disclosure in detail.

Here, the fixing member disclosed herein is used, for example, for joining two articles or for joining two physically separated parts of one article by deforming the article. Further, the fixing member disclosed herein may be used alone as one article in an application in which two different parts of the fixing member are joined together. In addition, the laminated body disclosed herein comprises a fixing member and a substrate.

(Fixing Member)

The fixing member disclosed herein comprises a surface having a coefficient of kinetic friction of 1.50 or less, an arithmetic mean roughness Ra of 5.00 μm or less, and a shear stress at the time of self-attachment of 100.00 N or more. Since the surface of the fixing member disclosed herein has a coefficient of kinetic friction not greater than the above-mentioned value and an arithmetic mean roughness Ra not less than the above-mentioned value, foreign substances such as paper scraps and specks of lint are unlikely to adhere to the surface even when in contact with the surface. On the other hand, since the shear stress of the fixing member generated at the time of self-attachment is not less than the above-mentioned value, when two such fixing members are used for joining, separation between the fixing members due to lateral displacement can be suppressed.

<Coefficient of Kinetic Friction of the Surface>

As described above, the kinematic coefficient of friction of the surface of the fixing member needs to be 1.50 or less, and it is preferably 1.30 or less, more preferably 1.10 or less, still more preferably 0.80 or less, and particularly preferably 0.54 or less, and it is preferably 0.10 or more, more preferably 0.20 or more, still more preferably 0.30 or more, and particularly preferably 0.35 or more. If the coefficient of kinetic friction exceeds 1.50, the adhesion of foreign substances to the fixing member cannot be suppressed. On the other hand, if the coefficient of kinetic friction is 0.10 or higher, even when a pair of fixing members in a jointed state are subjected to impact, lateral displacement of the fixing members will be further prevented and they will not be separated unintentionally.

The coefficient of kinetic friction of the surface of the fixing member can be adjusted, for example, by changing the components of the resin composition used to prepare the fixing member, or by changing the preparation conditions when preparing the fixing member. Specifically, the coefficient of kinetic friction can be lowered by blending a surface modifier, such as a silicone-based surface modifier, into the resin composition used to prepare the fixing member.

<Arithmetic Mean Roughness Ra of the Surface>

As described above, the arithmetic mean roughness Ra of the surface of the fixing member needs to be 5.00 μm or less, and it is preferably 4.00 μm or less, more preferably 3.00 μm or less, even more preferably 2.00 μm or less, and particularly preferably 1.80 μm or less, and it is preferably 0.05 μm or more, more preferably 0.10 μm or more, even more preferably 0.20 μm or more, and particularly preferably 0.40 μm or more. If the arithmetic mean roughness Ra of the surface exceeds 5.00 μm, the adhesion of foreign substances to the surface cannot be suppressed, because, presumably, foreign substances are more easily trapped in irregularities on the surface of the fixing member. On the other hand, if the arithmetic mean roughness Ra of the surface is 0.05 μm or more, even when a pair of fixing members in a joined state are subjected to impact, lateral displacement of the fixing members will be further prevented and they will not be separated unintentionally.

The arithmetic mean roughness Ra of the surface of the fixing member can be adjusted, for example, by changing the components of the resin composition used to prepare the fixing member, or by changing the preparation conditions when preparing the fixing member. Specifically, the arithmetic mean roughness Ra can be adjusted by changing the conditions for preparing the fixing member, such as the coating conditions for supplying the resin composition to the substrate and the curing conditions for turning the resin composition on the substrate into a cured product.

<Shear Stress Generated at the Time of Self-Attachment>

As described above, the shear stress of the fixing member generated at the time of self-attachment needs to be 100.00 N or more, and it is preferably 110.00 N or more, more preferably 120.00 N or more, and even more preferably 125.00 N or more. If the shear stress generated at the time of self-attachment is less than 100.00 N, lateral displacement of the fixing members in a joined state cannot be sufficiently prevented, causing the fixing members to be easily separated from each other. On the other hand, the upper limit for the shear stress of the fixing member generated at the time of self-attachment is not limited, yet is, for example, 200.00 N or less.

The sheer stress of the fixing member generated at the time of self-attachment can be adjusted, for example, by changing the components of the resin composition used to prepare the fixing member, or by changing the preparation conditions when preparing the fixing member. Specifically, the shear stress can be increased by reducing the amount of the curing agent in the resin composition used to prepare the fixing member.

<Surface Tackiness>

In addition, the fixing member has a surface tackiness of preferably 1.60 N or less, more preferably 1.47 N or less, even more preferably 1.35 N or less, and particularly preferably 0.99 N or less, and it is preferably 0.10 N or more. If the tackiness of the fixing member is 1.60 N or less, the adhesion of foreign substances to the fixing member can be sufficiently suppressed. On the other hand, if the tackiness of the fixing member is 0.10 N or more, good adhesion between such fixing members can be sufficiently facilitated.

The tackiness of the fixing member can be adjusted, for example, by changing the components of the resin composition used to prepare the fixing member, or by changing the preparation conditions for preparing the fixing member. For example, the tackiness can be reduced by increasing the amount of the curing agent in the resin composition used to prepare the fixing material.

<Composition and Preparation Method of the Fixing Member>

The fixing member is not particularly limited as long as it has the above-mentioned properties and can be formed from any material. However, the fixing member may preferably be obtained from a resin (i.e., made of a resin). For example, the fixing member may be a cured product of a resin composition containing a resin. More specifically, the fixing member may be obtained, for example, by curing a resin composition that contains a resin, a curing agent capable of curing the resin, and a silicone-based surface modifier. The resin composition may contain additives other than a resin, a curing agent, and a silicone-based surface modifier (other additives).

<<Resin>>

From the viewpoint of further suppressing separation between fixing members due to lateral displacement when the fixing members are attached together to form a joined state, preferred examples of the resin include, but are not limited to, a (meth)acrylic acid ester copolymer resin, a polyurethane resin, a polyester resin, and a urethane acrylate resin. These resins may be used alone or in combination of two or more. From the viewpoint of easily obtaining a thin fixing member, preferred as the resin is a urethane acrylate-based resin, and more preferred is a UV-curable urethane acrylate-based resin.

As used herein, "(meth)acryl" is used to indicate "acryl" and/or "methacryl".

The resin has a glass transition temperature of preferably −30° C. or higher, and of preferably 5° C. or lower and more preferably 0° C. or lower. If the glass transition temperature of the resin is −30° C. or higher, the adhesive force in the direction perpendicular to the joining surfaces will not be excessively increased between the joined fixing members. On the other hand, when the glass-transition temperature of the resin is 5° C. or lower, even in a cold environment, abutment between the fixing members can develop a sufficiently high adhesive force when the fixing members are abutted against each other, and the fixing members can be joined well.

In the present disclosure, the glass transition temperature of the resin can b e measured in accordance with JIS K 7121.

<<Curing Agent>>

The curing agent is not particularly limited as long as it can cure the above-mentioned resin, and may be, for example, a known cross-linking agent or photopolymerization initiator.

Specifically, examples of the curing agent include multifunctional acrylate-based crosslinking agents such as trimethylolpropane triacrylate and trimethylolpropane ethylene oxide-modified triacrylate; carbodiimide-based crosslinking agents; epoxy-based crosslinking agents such as polyethylene glycol diglycidyl ether, glycerol polyglycidyl ether, sorbitol polyglycidyl ether, and bisphenol A polyglycidyl ether; aziridine-based crosslinking agents such as ethyleneimine derivatives of aldehydes (e.g., acrolein); polyfunctional isocyanate-based crosslinking agents such as tolylene diisocyanate, trimethylolpropane tolylene diisocyanate, and diphenylmethanetriisocyanate; oxazoline-based crosslinking agents; metal salt crosslinking agents; metal chelate crosslinking agents; peroxide crosslinking agents; and photopolymerization initiators such as benzophenone-, acetophenone-, thioxanthone-, sulfonium-, and iodonium-based photopolymerization initiators. The curing agent may be used alone or in combination of two or more. From the viewpoint of further suppressing the adhesion of foreign substances to the fixing member, preferred as the curing agent is a multifunctional acrylate crosslinking agent, more preferred are trimethylolpropane triacrylate and trimethylolpropane ethylene oxide-modified triacrylate, and even more preferred is trimethylolpropane triacrylate.

The resin composition contains the curing agent in an amount of preferably 6 parts by mass or more, more preferably 7 parts by mass or more, even more preferably 8 parts by mass or more, still more preferably 10 parts by mass or more, and particularly preferably 11 parts by mass or more per 100 parts by mass of the resin, and of preferably 20 parts by mass or less, more preferably 19 parts by mass or less, even more preferably 16 parts by mass or less, and still more preferably 15 parts by mass or less per 100 parts by mass of the resin. If the content of the curing agent in the resin composition is 6 parts by mass or more per 100 parts by mass of the resin, the strength of the fixing member as the cured product of the resin composition can be secured and the adhesion of foreign substances to the fixing member can be further suppressed. On the other hand, if the content of the curing agent in the resin composition is 20 parts by mass or less per 100 parts by mass of the resin, lateral displacement of the fixing members as the cured products of the resin composition can be further suppressed.

<<Silicone-Based Surface Modifier>>

It is preferred that the resin composition contains a silicone-based surface modifier. Here, examples of the silicone surface modifier include polymers with a polysiloxane structure such as polydimethylsiloxane, polydiethylsiloxane, and poly(methylethyl) siloxane, as well as modified products of these polymers. Note that the silicone-based surface modifiers may be used alone or in combination of two or more. From the viewpoint of further suppressing the adhesion of foreign substances to the fixing member, particularly preferred as the silicone-based surface modifier are polydimethylsiloxane and modified products thereof (polydimethylsiloxane-based surface modifiers).

The resin composition contains the silicone-based surface modifier in an amount of preferably 0.05 parts by mass or more, more preferably 0.1 parts by mass or more, and even more preferably 0.15 parts by mass or more per 100 parts by mass of the resin, and of preferably 1.7 parts by mass or less, more preferably 0.6 parts by mass or less, and even more preferably 0.4 parts by mass or less, and particularly preferably 0.3 parts by mass or less per 100 parts by mass of the resin. If the content of the silicone-based surface modifier in the resin composition is 0.05 parts by mass or more per 100 parts by mass of the resin, the adhesion of foreign substances to the fixing members as the cured products of the resin composition can be further suppressed. In addition, lateral displacement of the fixing members as the cured products of the resin composition can be further suppressed because, presumably, the silicone-based surface modifier contained in the fixing members increases the affinity between the fixing members. On the other hand, if the content of the silicone-based surface modifier in the resin composition is 1.7 parts by mass or less per 100 parts by mass of the resin, the problem of increased slipperiness between the fixing members, which would otherwise occur when the amount of the silicone-based surface modifier in the fixing members is excessive, does not occur. In this way, lateral displacement of the fixing members as the cured products of the resin composition can be further suppressed.

The fixing member according to the present disclosure contains the silicone-based surface modifier in an amount of preferably 0.05 mass % or more and more preferably 0.07 mass % or more per 100 mass % of the fixing member, and of preferably 1.50 mass % or less, more preferably 0.50 mass % or less, and even more preferably 0.30 mass % or less. If the percentage of the silicone-based surface modifier in each fixing member is 0.05 mass % or more, adhesion of foreign substances to the fixing members and lateral displacement of the fixing members can be further suppressed. On the other hand, if the percentage of the silicone-based surface modifier in each fixing member is 1.50 mass % or less, lateral displacement of the fixing members can be further suppressed.

In the present disclosure, the percentage of the silicone-based surface modifier in the fixing member can be measured using a nuclear magnetic resonance (NMR) method as described in the EXAMPLES section below.

<<Other Additives>>

Other additives that the resin composition may optionally contain are not limited, and known additives can be used. Known additives include, for example, foaming agents, foaming aids, thickeners, fillers, preservatives, antifungal agents, gelling agents, flame retardants, anti-aging agents, antioxidants, tackifiers, photosensitizers, and conductive compounds. These are not limiting examples, and those described in WO2017/188118, for example, can be used. These additives may be used alone or in combination of two or more.

<<Preparation and Curing of the Resin Composition>>

The method of preparing the resin composition is not particularly limited, and the resin composition is obtainable by mixing the above-described respective components in a known manner. The method of curing the resin composition is also not particularly limited, and the resin composition can be cured by a known method such as UV irradiation. Although the resin composition can be foamed prior to curing, it is preferable that the resin composition not be foamed in the present disclosure. This is because the fixing member obtained as a cured product after undergoing the process of foaming the resin composition may also lose transparency, and the foaming may form fine irregularities on its surface, with the result that the surface may have an excessively high arithmetic mean roughness Ra and an increased amount of foreign substances adhered thereto.

Although the shape of the fixing member obtained for example as described above is not particularly limited, from the viewpoint of reducing the weight of the fixing member and securing the abutment area between such fixing members, it is preferable that the fixing member be a film member of any shape such as a strip- or sheet-like shape.

Although the thickness of the fixing member is not particularly limited, it is preferable to be 5 μm or more and 50 μm or less from the viewpoint of reducing the weight and securing the strength of the fixing member.

(Laminated Body)

The laminated body according to the present disclosure comprises at least a substrate and a fixing member. Note that the laminated body may also comprise a member other than the substrate and the fixing member.

First Embodiment of the Laminated Body

In a first embodiment of the laminated body disclosed herein, the laminated body comprises a substrate and any of the above-described fixing members according to the present disclosure. According to the first embodiment of the laminated body disclosed herein, when the fixing members are attached together to form a joined state, separation of the fixing members due to lateral displacement is suppressed and foreign substances are unlikely to adhere to the surfaces of the fixing members.

<<Substrate>>

In the first embodiment of the laminated body, the substrate is not limited and can be made of any material. For example, the substrate may be a substrate made of a resin including rubber (a resin substrate), a substrate made of metal (a metal substrate), a substrate made of paper (a paper substrate), or a substrate made of fiber (a fabric substrate). In addition, the substrate preferably has flexibility.

The shape of the substrate is also not particularly limited, and may be selected as appropriate according to the type of article to be fixed using the fixing member. For example, if the object to be fixed using the fixing member is a tape body (a strip-like article having an elongated shape) such as a tourniquet, a strip-like material may be used as the substrate.

The thickness of the substrate is also not particularly limited, and may be selected as appropriate according to the type of article and the like, as in the shape of the substrate.

<<Fixing Member>>

In the first embodiment of the laminated body disclosed herein, the fixing member is any of the fixing members disclosed herein.

Structural Examples of the Laminated Body in the First Embodiment

Structural examples of the laminated body in the first embodiment will be described below with reference to the drawings. However, the laminated body in this embodiment is not so limited.

First Example

In a first example of the first embodiment, the laminated body according to the present disclosure comprises a substrate and at least a pair of any of the fixing members disclosed herein. In this example, the two fixing members constituting the pair of fixing members are arranged in such a way that they are abuttable against each other as the substrate is bent and deformed.

For example, as an example of the first embodiment, FIG. 1A illustrates a laminated body 10 that comprises a strip-like substrate 11 and a pair of fixing members (fixing members 12a and 12b). The fixing member 12a is located at one end of the substrate 11 in the longitudinal direction, and the fixing member 12b at the other end of the substrate 11 in the longitudinal direction. The fixing members 12a and 12b are located on opposite surfaces of the substrate 11 from each other (i.e., the fixing member 12a is located on one surface of the strip-like substrate 11 and the fixing member 12 on the other surface).

As used herein, an "end" in the "longitudinal direction" of the substrate refers to a region where the distance from the longitudinal center line (a straight line passing through the longitudinal center and perpendicular to the longitudinal axis) of the substrate is 30% or more of the longitudinal width.

Figure 1B:
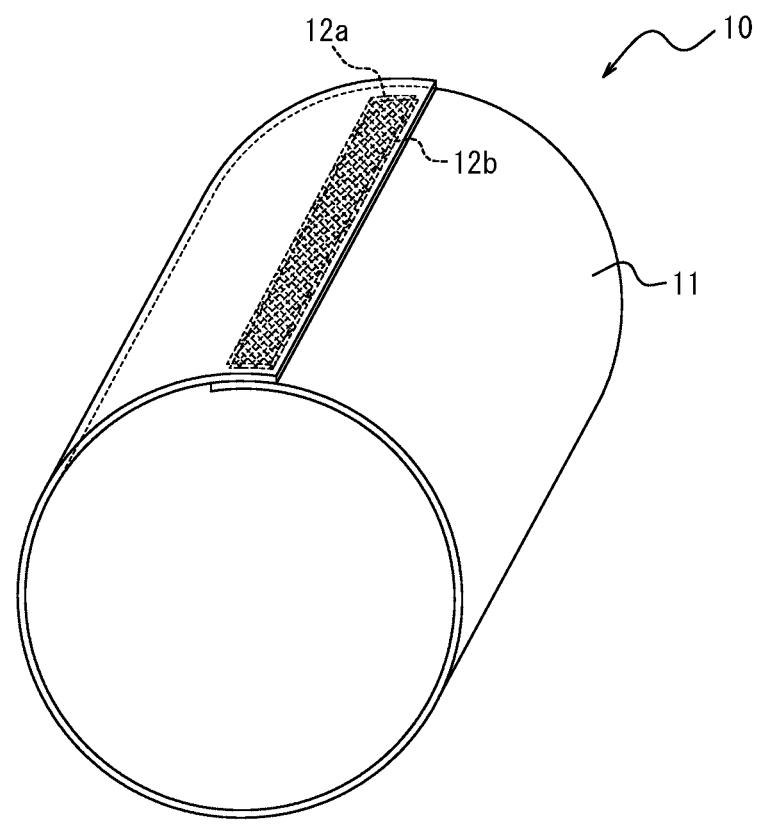
FIG. 1B is a perspective view illustrating a state in which fixing members of the laminated body 10 are joined together.

As illustrated in FIG. 1B, the substrate 11 can be bent and deformed to join the fixing members of the laminated body 10 (i.e., the fixing members 12a and 12b) together.

Figure 2A:
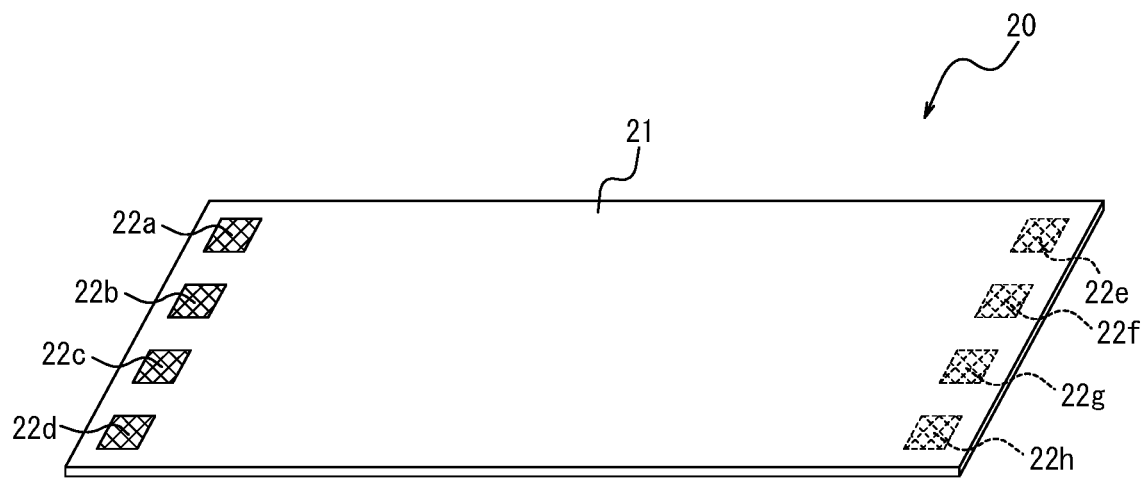
FIG. 2A is a perspective view of a laminated body 20, which is an example of an embodiment of the laminated body according to the present disclosure.

In addition, for example, as another example of the first embodiment, FIG. 2A illustrates a laminated body 20 that comprises a strip-like substrate 21 and four pairs of fixing members (fixing members 22a and 22e, fixing members 22b and 22f, fixing members 22c and 22g, and fixing members 22d and 22h). The fixing members 22a-22d are located at one end of the substrate 21 in the longitudinal direction, and the fixing members 22e-22h at the other end of the substrate 21 in the longitudinal direction. The fixing members 22a-22d and 22e-22h are located on opposite surfaces of the substrate 11 from one another (i.e., the fixing members 22a-22d are located on one surface of the strip-like substrate 21, and the fixing members 22e-22h on the other surface of the strip-like substrate 21).

Figure 2B:
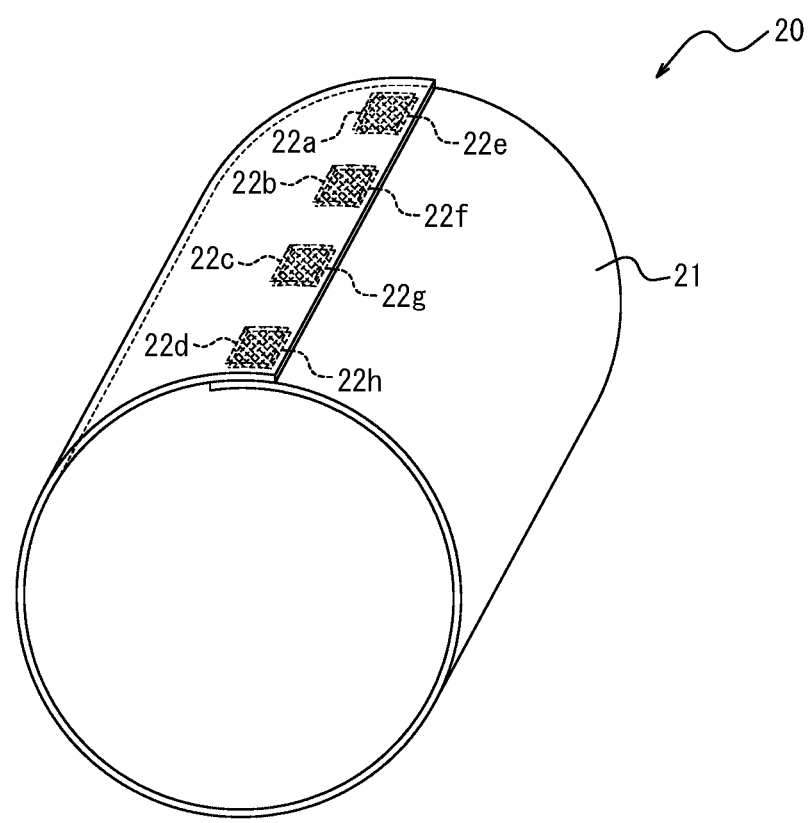
FIG. 2B is a perspective view illustrating a state in which fixing members of the laminated body 20 are joined together.

Then, as illustrated in FIG. 2B, the substrate 21 can be bent and deformed to respectively join the fixing members of the laminated body 20 (i.e., the fixing members 22a and 22e, 22b and 22f, 22c and 22g, and 22d and 22h) together.

In the laminated body 10 in FIGS. 1A-1B, one fixing member is arranged at each end of the substrate 11, and in the laminated body 20 in FIGS. 2A-2B, four fixing members are arranged at each end of the substrate 21. However, the number of fixing members arranged at each end is not so limited. In the laminated body 10 of FIGS. 1A-1B and the laminated body 20 of FIGS. 2A-2B, the fixing member(s) at one end and the fixing member(s) at the other end are located on opposite sides of the strip-like substrate from each other. However, the fixing member(s) at one end and the fixing member(s) at the other end may be located on the same surface of the strip-like substrate.

Second Example

In a second example of the first embodiment, the laminated body according to the present disclosure comprises a substrate and at least one of the fixing members disclosed herein. In this example, the laminated body can be joined to another fixing member through its own fixing member.

Figure 3A:
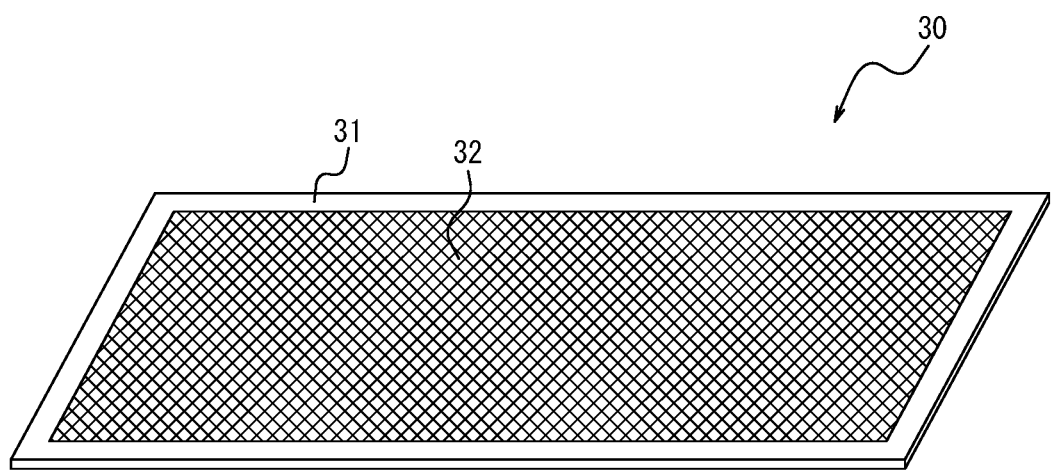
FIG. 3A is a perspective view of a laminated body 30, which is an example of an embodiment of the laminated body according to the present disclosure.
Figure 3B:
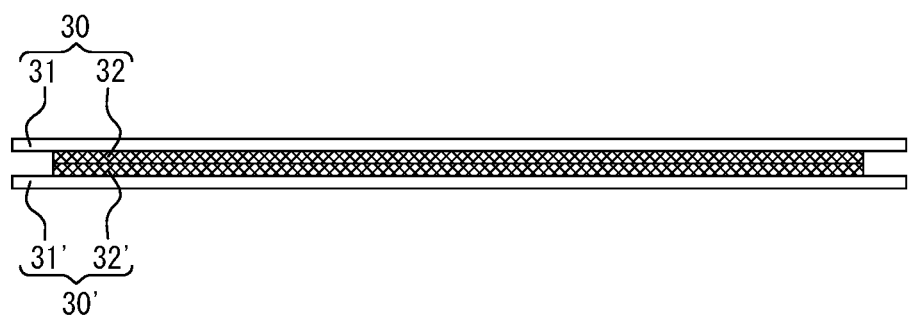
FIG. 3B is a cross-sectional view illustrating a state in which a laminated body 30 and a laminated body 30' are joined together via fixing members.

For example, as another example of the first embodiment, FIG. 3A illustrates a laminated body 30 that comprises a sheet-like substrate 31 and a fixing member 32. The laminated body 30 can be joined via the fixing member 32 to another laminated body 30' comprising a substrate 31' and a fixing member 32', for example, as illustrated in FIG. 3B.

Figure 4A:
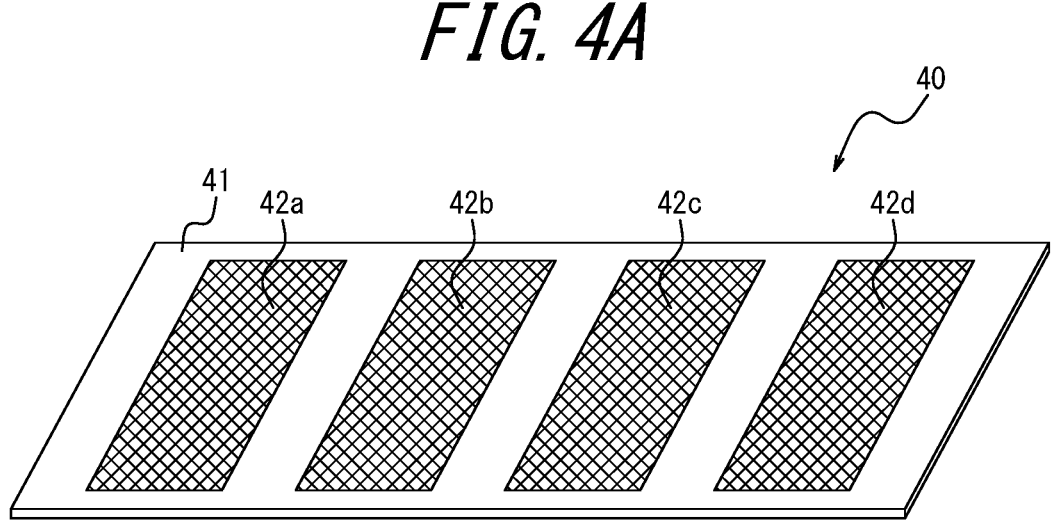
FIG. 4A is a perspective view of a laminated body 40, which is an example of an embodiment of the laminated body according to the present disclosure.
Figure 4B:
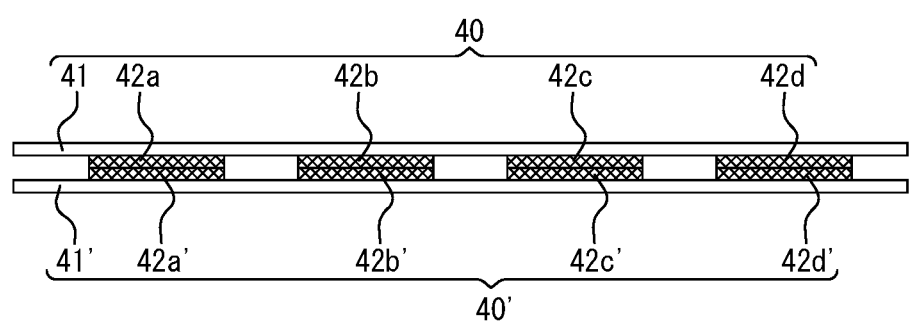
FIG. 4B is a cross-sectional view illustrating a state in which a laminated body 40 and a laminated body 40' are joined together via fixing members.

In addition, for example, as another example of the first embodiment, FIG. 4A illustrates a laminated body 40 that comprises a sheet-like substrate 41 and fixing members 42a, 42b, 42c, 42d. The laminated body 40 can be joined via the fixing members 42a, 42b, 42c, 42d to another laminated body 40' comprising a substrate 41' and fixing members 42a', 42b', 42c', 42d', for example, as illustrated in FIG. 4B.

Second Embodiment of the Laminated Body

In a second embodiment of the laminated body disclosed herein, the laminated body comprises at least a substrate, a first fixing member located on the substrate, and a second fixing member located on the substrate. The first fixing member and the second fixing member are positioned to be abuttable against each other. The surfaces of the first and second fixing members each need to have a coefficient of kinetic friction of 1.50 or less, and an arithmetic mean roughness Ra of 5.00 µm or less. Furthermore, a shear stress generated when the first and second fixing members are attached together needs to be 100.00 N or more.

According to the second embodiment of the laminated body disclosed herein, since the surface of each fixing member has a coefficient of kinetic friction not greater than the above-mentioned value and an arithmetic mean roughness Ra not greater than the above-mentioned value, foreign substances such as paper scraps and specks of lint are unlikely to adhere to the surface even when in contact with the surface. On the other hand, since the shear stress of the laminated body generated at the time of attaching the pair of fixing members together is not less than the above-mentioned value, separation between the fixing members due to lateral displacement can be suppressed.

<<Substrate>>

In the second embodiment of the laminated body, the substrate is not particularly limited, and may be the one described above in the section "First Embodiment of the Laminate".

<<Fixing Member>>

In the second embodiment of the laminated body, the first and second fixing members, as described above, each have a coefficient of kinetic friction of 1.50 or less and an arithmetic mean roughness Ra of 5.00 μm or less. A shear stress generated when the first and second fixing members are attached together is 100.00 N or more.

[Coefficient of Kinetic Friction and Arithmetic Mean Roughness Ra of the Surface]

In the second embodiment of the laminated body, the preferred upper and lower limits for the coefficient of kinetic friction and the arithmetic mean roughness Ra of the surface of each of the first and second fixing members as well as the reasons thereof are the same as those of the "fixing member" of the present disclosure described above.

[Shear Stress when the First and Second Fixing Members are Attached Together]

The shear stress generated when the first and second fixing members are attached together needs to be 100.00 N or more as described above, and it is preferably 110.00 N or more, more preferably 120.00 N or more, and even more preferably 125.00 N or more. If the shear stress generated when the first and second fixing members are attached together is less than 100.00 N, lateral displacement of the fixing members in a joined state cannot be sufficiently prevented, and these fixing members are easily separated from each other. On the other hand, the upper limit for the shear stress generated when the first and second fixing members are attached together is not limited, yet is, for example, 200.00 N or less.

The shear stress when the first and second fixing members are attached together can be adjusted, for example, by changing the components of the resin composition used to prepare the first and second fixing members, or by changing the preparation conditions when preparing the first and second fixing members. Specifically, the shear stress can be improved by using the same or similar (in terms of monomer composition, etc.) resin as the resin in the resin composition used to prepare the two fixing members. In addition, the shear stress can be increased by reducing the amount of the curing agent in the resin composition used to prepare the fixing members.

[Surface Tackiness]

In the second embodiment of the laminated body, the preferred upper and lower limits for the surface tackiness of the first and second fixing members as well as the reasons thereof are the same as those of the "fixing member" of the present disclosure described above.

[Composition and other characteristics of the First and Second Fixing Members]

In addition, suitable examples and suitable blending amounts of various components (such as a resin, a curing agent, and a silicone-based surface modifier) that may be contained in the resin composition used to prepare each of the first and second fixing members, as well as the preparation and curing methods of the resin composition for each of the first and second fixing members, are the same as those for the "fixing member" of the present disclosure described above.

<Structural Example of the Laminated Body in the Second Embodiment>>

Structural examples of the laminated body in the second embodiment include those illustrated in FIGS. 1A-1B and 2A-2B in the section "First Embodiment of the Laminated Body". Structural examples of the laminated body in the second embodiment will be described below with reference to the drawings. However, the laminated body in this embodiment is not so limited.

Specifically, in the case of adopting the laminated body 10 in FIG. 1A as the structure of the laminated body in the second embodiment, for example, the first fixing member can be the fixing member 12a in FIG. 1A and the second fixing member be the fixing member 12b in FIG. 1A. As illustrated in FIG. 1B, the substrate 11 can be bent and deformed to join the first and second fixing members of the laminated body 10 (i.e., the fixing members 12a and 12b).

Alternatively, in the case of adopting the laminated body 20 in FIG. 2A as the structure of the laminated body in the second embodiment, at least one of the combinations of fixing members 22a and 22e, fixing members 22b and 22f, fixing members 22c and 22g, or fixing members 22d and 22h in FIG. 2A can be used as the first and second fixing members. As illustrated in FIG. 2B, the substrate 21 can be bent and deformed to join the first and second fixing members of the laminated body 20 (i.e., at least one combination of fixing members 22a and 22e, 22b and 22f, 22c and 22g, or 22d and 22h).

<<Method of Producing the Laminated Body>>

The method of producing the laminated body is not particularly limited, yet for example, such laminated body comprising a substrate and a fixing member bonded and fixed to the substrate is obtainable by curing a resin composition coated directly onto the substrate. Such a laminated body is also obtainable by curing the resin composition coated on a known releasable substrate to form a fixing member thereon, and transferring the fixing member onto a substrate.

Although some embodiments of the laminated body according to the present disclosure have been described above based on specific examples, the laminated body according to the present disclosure is by no means limited thereto.

(Applications of the Fixing Member and the Laminated Body)

The applications of the fixing member and laminated body disclosed herein are not particularly limited. For example, the fixing member and laminated body disclosed herein can be used for tourniquets, sock bands, belts, furniture anchoring parts for earthquakes, touch fasteners for clothing, tableware and/or cup holders (in trains, airplanes, etc.), load displacement prevention members, and temporary fixing members during the manufacture of electronic components such as semiconductors and transistors.

In addition, containers (e.g., cigarette containers, confectionery containers, coffee containers, tea containers, and detergent containers) may be excluded from the applications of the fixing member and laminated body disclosed herein.

EXAMPLES

The following provides more specific description of the present disclosure with reference to examples. However, the present disclosure is not limited to these examples. In the following description, "%" and "parts" used in expressing quantities are by mass, unless otherwise specified. In the examples and comparative examples, the coefficient of kinetic friction and the arithmetic mean roughness Ra of the surface of each fixing member, the surface tackiness of each fixing member, the shear stress generated when fixing members are attached together, the percentage of the silicone-based surface modifier in each fixing member, and the resistance to lateral displacement of fixing members of tourniquets and the difficulty in adhesion of foreign substances to the fixing members were measured and evaluated as follows. The results are all listed in Tables 1 and 2.

<Coefficient of Kinetic Friction of the Surface>

In accordance with JIS K 7125, laminated bodies A were used to measure the coefficient of kinetic friction between a sheet of carton paper and the fixing member of each laminated body A in the following way.

First, a 63 mm×63 mm sliding piece (weight: 1.96 N) was attached to a sheet of carton paper (size: 63 mm×63 mm, product name: "OK Ball" manufactured by Oji Materia Co. Ltd., grammage: 230 g/m$^2$) using double-sided adhesive tape "Nice Tack NW-15S" manufactured by Nichiban Co., Ltd. Then, as illustrated in FIG. 5, the obtained attached body of the carton paper 52 and the sliding piece 53 was set on each of the laminated bodies 50 (laminated bodies A, each comprising a fixing member 51 and a sheet of carton paper 52 as a substrate) prepared in the examples and comparative examples such that the carton paper 52 side of the attached body was in contact with the fixing member 51 side of the laminated body 50. The force of kinetic friction generated when the sliding piece 53 was pulled horizontally at a speed of 500 mm/min in an environment of 23° C. and 50% RH was measured using a tensile testing machine ("Autograph AG-IS" manufactured by Shimadzu Corporation; the entire machine is not shown) equipped with a load cell 54, and the coefficient of kinetic friction was calculated by:

coefficient of kinetic friction [—]=force of kinetic friction [N]/1.96[N].

<Arithmetic Mean Roughness Ra of the Surface>

In accordance with HS B 06010-2001, laminated bodies A were used to measure the arithmetic mean roughness Ra of the surface of the fixing member of each laminated body A.

Specifically, using a shape measurement laser microscope ("VK-X100" manufactured by Keyence Corporation), a roughness curve was drawn for the surface on the fixing member side of each of the laminated bodies (laminated bodies A, each comprising a fixing member and a sheet of carton paper as a substrate) prepared in the examples and comparative examples, and the arithmetic mean roughness Ra of the surface was calculated by the following formula. In the formula, Lr represents the measurement length and Zn represents the height of the nth measurement line when the height of the average line of the curve is 0.

$$Ra = \frac{1}{Lr}\int_0^{Lr} |Zn|dx$$

<Shear Stress>

Figure 6:
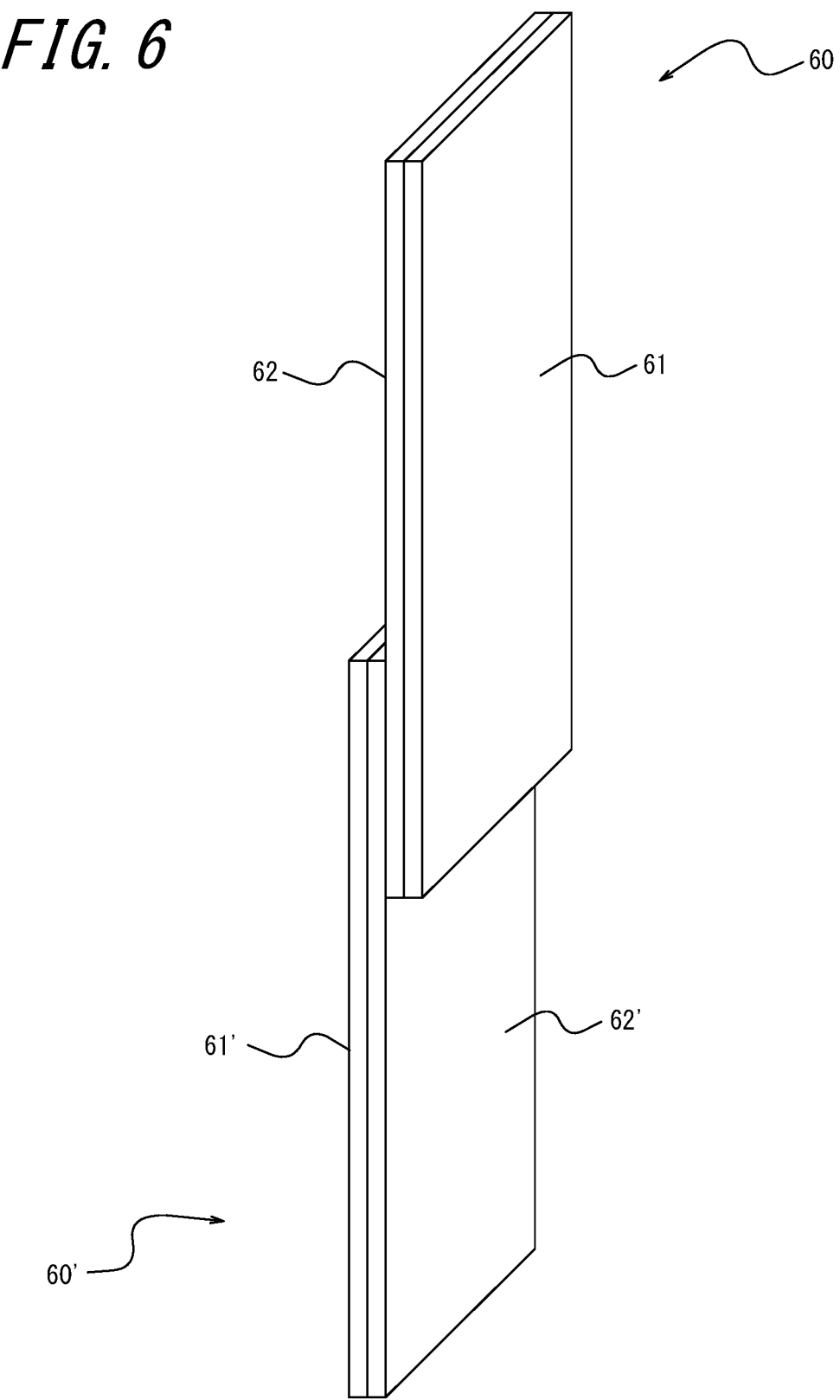
FIG. 6 is a perspective view schematically illustrating an operation to measure the shear stress generated when two fixing members are attached together.

Two cut-out pieces with a size of 25 mm in width and 120 mm in length were cut out from each of the laminated bodies B prepared in the examples and comparative examples. Then, as illustrated in FIG. 6, the two cut-out pieces (cut-out piece 60 and cut-out piece 60') were attached together such that respective fixing members (fixing member 62 and fixing member 62') were in contact with each other at respective ends within a range of 25 mm in width and 25 mm in length, and the resulting attached body was crimped by making one round trip with a 2.0 kgf (19.6133 N) load roller, yielding a specimen. Then, in an environment of 23° C. and 50% RH, the maximum load when each obtained specimen was pulled in the longitudinal direction with a tensile testing machine ("AUTOGRAPH AG-IS20KN" manufactured by Shimadzu Corporation) at a speed of 300 mm/min was measured as shear stress.

<Surface Tackiness>

The surface tackiness of each fixing member was measured using a probe tack tester ("TAC1000" manufactured by RHESCA Co., Ltd.). Specifically, in an environment of 23° C. and 50% RH, a flat probe tip of 10 mm in diameter was pressed against the fixing member side of each laminated body A with a load of 0.5 N for 5 seconds, and the force required to pull the probe away from the fixing member of the laminated body A at a speed of 15 mm/min was measured, and the measurement result was used as the surface tackiness of the fixing member.

<Percentage of the Silicone-Based Surface Modifier in the Fixing Member>

Each of the fixing members prepared in the examples and comparative examples was impregnated with hexane and subjected to an 8-hour extraction operation at 60° C., and $^1$H-NMR measurements were performed using deuterated chloroform without tetramethylsilane (TMS) as a reference material. From the measurement results obtained, a calibration curve was prepared from the ratio of the intensity of residual CHCl in deuterated chloroform to the intensity of silicon-derived $CH_3$—Si, and the amount (%) of the silicone-based surface modifier in 100% of each fixing member was quantified.

<Resistance to Lateral Displacement of the Fixing Members>

Two cut-out pieces with a size of 25 mm in width and 120 mm in length were cut out from each of the laminated bodies B prepared in the examples and comparative examples. Then, as illustrated in FIG. 6, the two cut-out pieces (cut-out piece 60 and cut-out piece 60') were attached together such that respective fixing members (fixing member 62 and fixing member 62') were in contact with each other at respective ends within a range of 25 mm in width and 25 mm in length, and the resulting attached body was crimped on top and bottom by making one round trip with a 2.0 kgf (19.6133 N) load roller, yielding a specimen. For each obtained specimen, the edges of the fixing members on the unattached side were pinched with the fingers, and the resistance to lateral displacement of the fixing members when pulled away from each other in the longitudinal direction was evaluated according to the following criteria.

A: Fixing members stuck to each other, and were not displaced laterally at all even when pulled forcefully.

B: Fixing materials stuck to each other, but were displaced laterally when pulled forcefully.
C: Fixing members stuck to each other, but were easily displaced laterally.
D: Fixing members did not stick to each other and were displaced laterally.

<Difficulty in Adhesion of Foreign Substances to the Fixing Member>

After sprinkling specks of lint on the fixing member of each of the laminated bodies A obtained in the examples and comparative examples, and tapping it from the carton paper side, evaluation was made according to the following criteria. Note that lint is just one example of foreign substances that is most likely to adhere to the fixing member.

A: There was no lint (foreign substance) adhered to the fixing member.
B: A small amount of lint (foreign substance) adhered to the fixing member, but was easy to remove.
C: Lint (foreign substance) adhered to the fixing member, and was somewhat difficult to remove.
D: Lint (foreign substance) adhered to the fixing member, and could not be removed.

Example 1

<Preparation of Resin Composition>

A mixing vessel was charged with 100 parts of a UV-curable urethane acrylate-based resin A (storage modulus E' at 25° C.=0.6 MPa, Tg=−23° C.) as a resin, 10 parts of trimethylolpropane triacrylate as a curing agent, and 0.1 parts of polyether-modified polydimethylsiloxane (manufactured by BYK) as a silicone-based surface modifier. The contents of the mixing vessel were stirred with a magnetic stirrer for 5 minutes to obtain a resin composition.

<Preparation of a Laminated Body A formed from a Fixing Member and a Substrate (Carton Paper)>

Each resin composition thus obtained was applied using a wire bar onto a sheet of carton paper as a substrate (thickness: 285 μm, product name: "OK Ball" manufactured by Oji Materia Co., Ltd., grammage: 230 g/m²). The substrate with the resin composition applied thereon was placed in a conveyor UV irradiation device (manufactured by Eye Graphics Co., Ltd.) set to the conditions of 2 KW lamp output of a high-pressure mercury lamp and a conveyor speed of 9 m/min. Then, the resin composition on the substrate was irradiated with ultraviolet light to cure the resin composition, and a laminated body A was obtained, which was equipped with a substrate and a fixing member (a resin adhesive layer) having a thickness of 25 μm on the substrate. In order to prevent the reaction from being inhibited by oxygen in the air, the oxygen concentration in the device was reduced to 500 ppm or less by purging with nitrogen.

<Preparation of a Laminated Body B formed from a Fixing member and a Substrate (PET Film with Corona-treated Surface)>

Each resin composition thus obtained was applied using a wire bar onto a smooth polyethylene terephthalate (PET) film with a corona-treated surface as a substrate (thickness: 50 μm, product name: "5-50" manufactured by Unitika Ltd.). The substrate with the resin composition applied thereon was placed in a conveyor UV irradiation device (manufactured by Eye Graphics Co., Ltd.) set to the conditions of 2 KW lamp output of a high-pressure mercury lamp and a conveyor speed of 9 m/min. Then, the resin composition on the substrate was irradiated with ultraviolet light to cure the resin composition, and a laminated body A comprising a substrate and a fixing member (a resin adhesive layer) having a thickness of 25 μm on the substrate was obtained. In order to prevent the reaction from being inhibited by oxygen in the air, the oxygen concentration in the device was reduced to 500 ppm or less by purging with nitrogen.

Examples 2, 3, and 10

Resin compositions and laminated bodies were prepared in the same manner as in Example 1, except that the amount of polyether-modified polydimethylsiloxane used was changed to 0.2 parts (Example 2), 0.4 parts (Example 3), and 1.5 parts (Example 10) in preparation of the resin compositions, and various measurements and evaluations were performed.

Example 4

A resin composition and a laminated body were prepared in the same manner as in Example 2, except that the amount of trimethylolpropane triacrylate used was changed to 7 parts and acrylic group-containing polyether-modified polydimethylsiloxane (manufactured by BYK) was used instead of polyether-modified polydimethylsiloxane in preparation of the resin composition, and various measurements and evaluations were performed.

Examples 5 and 6

Resin compositions and laminated bodies were prepared in the same manner as in Example 4, except that the amount of trimethylolpropane triacrylate used was changed to 10 parts (Example 5) and 12 parts (Example 6) in preparation of the resin compositions, and various measurements and evaluations were performed.

Example 7

A resin composition and a laminated body were prepared in the same manner as in Example 2, except that the amount of trimethylolpropane triacrylate used was changed to 15 parts in preparation of the resin composition, and various measurements and evaluations were performed.

Example 8

A resin composition and a laminated body were prepared in the same manner as in Example 7, except that trimethylolpropane ethylene oxide-modified triacrylate was used instead of trimethylolpropane triacrylate in preparation of the resin composition, and various measurements and evaluations were performed.

Example 9

A resin composition and a laminated body were prepared in the same manner as in Example 2, except that a UV-curable urethane acrylate-based resin B (storage modulus E' at 25° C.=3.5 MPa, Tg=0.6° C.) was used instead of the UV-curable urethane acrylate-based resin A in preparation of the resin composition, and various measurements and evaluations were performed.

Comparative Example 1

A resin composition and a laminated body were prepared in the same manner as in Example 2, except that the amount of trimethylolpropane triacrylate used was changed to 5 parts in preparation of the resin composition, and various measurements and evaluations were performed.

Comparative Example 2

A resin composition and a laminated body were prepared in the same manner as in Example 2, except that the amount of polyether-modified polydimethylsiloxane used was changed to 0.02 parts in preparation of the resin composition, and various measurements and evaluations were performed.

Comparative Example 3

<Preparation of a Resin Composition>

A mixing vessel was charged with 100 parts of an acrylic ester copolymer resin, 5 parts of a carbodiimide cross-linking agent (product name: "CARBODILITE® E-02" Nisshinbo Chemical Inc.; CARBODILITE is a registered trademark in Japan, other countries, or both), and 3.5 parts of a titanium dioxide water dispersion (product name: "DISPERSE WHITE HG-701" manufactured by DIC Corporation). The contents of the mixing vessel were stirred with a disper blade. Then, while continuing to stir, 6 parts of a foaming agent (a 1/1 (in mass ratio) mixture of a mixture of an amphoteric product of alkylbetaine and fatty acid alkanolamide (product name: "DICNAL M-20" manufactured by DIC Corporation)/a sulfonic acid type anionic surfactant (product name: "DICNAL M-40" manufactured by DIC Corporation)), and 0.6 parts of an ammonia solution were added, and finally 4.5 parts of a thickener (carboxylic acid-modified acrylic ester polymer, "B-300K", manufactured by Toagosei Co., Ltd.) was added. The obtained mixture was then filtered through 150 mesh. Finally, ammonia was added to adjust the viscosity to 5,000 mPa·s to obtain a resin composition.

The resin composition was stirred with a whisk to obtain an expansion ratio of 1.6 times, and stirring was further continued for 5 minutes at a reduced stirring speed to obtain a foamed resin composition.

<Preparation of a Laminated Body formed from a Fixing Member and a Substrate>

Each foamed resin composition thus obtained was applied onto a polyethylene terephthalate film as a substrate (thickness: 50 μm) using a 0.3 mm applicator. The resulting product was placed in a drying oven and held at 80° C. for 1.33 minutes, 120° C. for 1.33 minutes, and 140° C. for 1.33 minutes, whereby the resin composition was dried and cross-linked, and a laminated body comprising a substrate and a fixing member (resin adhesive layer) having a thickness of 180 μm on the substrate was obtained. Using the laminated bodies thus obtained, various measures and evaluations were performed.

In performing evaluations in the same way as in Example 1, in Comparative Example 3, a laminated body formed from a fixing member and a substrate (polyethylene terephthalate film) obtained as described above were used as the laminated bodies A and B in Example 1.

Comparative Example 4

<Preparation of Touch Fasteners>

As fixing members, touch fasteners (product name: "fastener tape" manufactured by Daiso Industries Co., Ltd., which is formed from a set of members, one having a loop surface and the other having a hook surface) were prepared.

Comparative Example 4-1 (Member Having a Loop Surface)

Using members having loop surfaces (touch fasteners) instead of laminated bodies, the coefficient of kinetic friction, arithmetic mean roughness Ra, and tackiness of the loop surfaces, as well as the shear stress generated when the loop surfaces of two such members were attached to each other, were measured. Evaluation was also made of the resistance to lateral displacement of members having loop surfaces instead of laminated bodies when the loop surfaces were attached to each other, and the difficulty in adhesion of foreign substances to the loop surfaces of the members.

Comparative Example 4-2 (Member Having a Hook Surface)

Using members having hook surfaces (touch fasteners) instead of laminated bodies, the coefficient of kinetic friction, arithmetic mean roughness Ra, and tackiness of the hook surfaces, as well as the shear stress generated when the hook surfaces of two such members were attached to each other, were measured. Evaluation was also made of the resistance to lateral displacement of members having hook surfaces instead of laminated bodies when the hook surfaces were attached to each other, and the difficulty in adhesion of foreign substances to the hook surfaces of the members.

Comparative Example 4-3 (Attachment of a Member Having a Loop Surface to a Member Having a Hook Surface)

Instead of laminated bodies, a member having a loop surface and a member having a hook surface were prepared, and the shear stress generated when the loop surface was attached to the hook surface was measured. Evaluation was also made of the resistance to lateral displacement of the members having loop and hook surfaces, respectively, instead of laminated bodies when the loop surface was attached to the hook surface.

Comparative Example 5

A resin composition and a laminated body were prepared in the same manner as in Example 2, except that the amount of trimethylolpropane triacrylate used was changed to 25 parts in preparation of the resin composition, and various measurements and evaluations were performed.

Comparative Example 6

A resin composition and a laminated body were prepared in the same manner as in Example 1, except that the amount of polyether-modified polydimethylsiloxane used was changed to 2 parts in preparation of the resin composition, and various measurements and evaluations were performed.

TABLE 1

|  |  |  | Example 1 | Example 2 | Example 3 | Example 4 | Example 5 | Example 6 | Example 7 | Example 8 | Example 9 | Example 10 |
|---|---|---|---|---|---|---|---|---|---|---|---|---|
| Resin composition | Resin | Urethane acrylate-based resin A [parts by mass] | 100 | 100 | 100 | 100 | 100 | 100 | 100 | 100 | — | 100 |
|  |  | Urethane acrylate-based resin B [parts by mass] | — | — | — | — | — | — | — | — | 100 | — |
|  |  | Acrylic acid ester copolymer resin [parts by mass] | — | — | — | — | — | — | — | — | — | — |
|  | Curing agent | Trimethylolpropane triacrylate [mass parts] | 10 | 10 | 10 | 7 | 10 | 12 | 15 | — | 10 | 10 |
|  |  | Trimethylolpropane ethylene oxide-modified triacrylate [parts by mass] | — | — | — | — | — | — | — | 15 | — | — |
|  |  | Carbodiimide-based crosslinking agent [parts by mass] | — | — | — | — | — | — | — | — | — | — |
|  | Silicone-based surface modifier | Polyether-modified polydimethylsiloxane [parts by mass] | 0.1 | 0.2 | 0.4 | — | — | — | 0.2 | 0.2 | 0.2 | 1.5 |
|  |  | Acrylic group-containing polyether-modified polydimethylsiloxane [parts by mass] | — | — | — | 0.2 | 0.2 | 0.2 | — | — | — | — |
| Fixing member | Percentage of silicone-based surface modifier [mass %] |  | 0.09 | 0.18 | 0.38 | 0.19 | 0.18 | 0.18 | 0.17 | 0.18 | 0.18 | 1.44 |
|  | Shear stress [N] |  | 125.95 | 127.32 | 137.77 | 140.84 | 133.42 | 125.98 | 128.82 | 125.66 | 128.92 | 129.27 |
|  | Coefficient of kinetic friction [-] |  | 0.95 | 0.71 | 0.55 | 0.80 | 0.69 | 0.53 | 0.36 | 0.58 | 0.38 | 0.35 |
|  | Arithmetic mean roughness Ra of surface [μm] |  | 1.49 | 0.88 | 1.23 | 0.66 | 1.41 | 0.91 | 1.79 | 1.21 | 1.35 | 1.05 |
|  | Tackiness [N] |  | 1.10 | 1.11 | 1.00 | 1.55 | 1.01 | 0.91 | 0.70 | 1.30 | 1.03 | 1.16 |
| Evaluation | Resistance to lateral displacement of fixing members |  | A | A | A | A | A | A | A | A | A | A |
|  | Difficulty of adhesion of substances to fixing member |  | B | B | B | B | B | A | A | B | B | B |

TABLE 2

|  |  |  | Comparative example 1 | Comparative example 2 | Comparative example 3 | Comparative example 4-1 | Comparative example 4-2 | Comparative example 4-3 | Comparative example 5 | Comparative example 6 |
|---|---|---|---|---|---|---|---|---|---|---|
|  |  |  |  |  |  | Touch fastener | | | | |
| Resin composition | Resin | Urethane acrylate-based resin A [parts by mass] | 100 | 100 | — | Loop surface | Hook surface | Loop surface and Hook surface | 100 | 100 |
|  |  | Urethane acrylate-based resin B [parts by mass] | — | — | — |  |  |  | — | — |
|  |  | Acrylic acid ester copolymer resin [parts by mass] | — | — | 100 |  |  |  | — | — |
|  | Curing agent | Trimethylolpropane triacrylate [parts by mass] | 5 | 10 | — |  |  |  | 25 | 10 |
|  |  | Trimethylolpropane ethylene oxide-modified triacrylate [parts by mass] | — | — | — |  |  |  | — | — |
|  |  | Carbodiimide-based crosslinking agent [parts by mass] | — | — | 5 |  |  |  | — | — |
|  | Silicone-based surface modifier | Polyether-modified polydimethylsiloxane [parts by mass] | 0.2 | 0.02 | — |  |  |  | 0.2 | 2 |
|  |  | Acrylic group-containing polyether-modified polydimethylsiloxane [parts by mass] | — | — | — |  |  |  | — | — |
| Fixing member | Percentage of silicone-based surface modifier [mass %] |  | 0.19 | 0.01 | 0 | 0 | 0 | Refer to the left column. | 0.19 | 1.92 |
|  | Shear stress [N] |  | 81.08 | 133.31 | 73.22 | 0.00 | 11.27 | 62.29 | 83.44 | 90.58 |
|  | Coefficient of kinetic friction [-] |  | 1.21 | 2.17 | 2.30 | 0.35 | 0.09 | Refer to the left column. | 0.23 | 0.25 |
|  | Arithmetic mean roughness Ra of surface [μm] |  | 1.03 | 1.13 | 5.83 | 413.18 | 300.32 |  | 1.33 | 1.01 |
|  | Tackiness [N] |  | 1.94 | 1.10 | 7.52 | 0.55 | 0.74 |  | 0.45 | 0.95 |

TABLE 2-continued

|  |  | Comparative example 1 | Comparative example 2 | Comparative example 3 | Comparative example 4-1 | Comparative example 4-2 | Comparative example 4-3 | Comparative example 5 | Comparative example 6 |
|---|---|---|---|---|---|---|---|---|---|
|  |  |  |  |  | Touch fastener | | | | |
| Evaluation | Resistance to lateral displacement of fixing members | C | A | C | D | C | B | C | C |
|  | Difficulty of adhesion of substances to fixing member | D | D | C | C | D | Refer to the left column. | A | A |

From Table 1, it can be seen that in Examples 1-10, in which each fixing member had a surface with a coefficient of kinetic friction and an arithmetic mean roughness Ra each being not greater than the predetermined values and with a shear stress at the time of self-attachment being not less than the predetermined value, adhesion of foreign substances to the fixing member was suppressed, and when such fixing members were joined together, lateral displacement of the fixing members was difficult to occur.

On the other hand, from Table 2, it can be seen that in Comparative Example 1, in which a fixing member with a shear stress at the time of self-attachment being less than the predetermined value was used, when such fixing members were joined together, lateral displacement of the fixing members could not be suppressed.

From Table 2, it can be seen that in Comparative Example 2, in which a fixing member having a surface with a coefficient of kinetic friction exceeding the predetermined value was used, adhesion of foreign substances to the fixing member could not be suppressed.

Furthermore, it can be seen that in Comparative Example 3 in Table 2, in which a fixing member having a surface with a kinetic coefficient of friction and an arithmetic mean roughness Ra each exceeding the predetermined values and with a shear stress at the time of self-attachment being less than the predetermined value were used, adhesion of foreign substances to the fixing member could not be suppressed, and when such fixing members were joined together, lateral displacement of the fixing members could not be suppressed.

From Table 2, it can be also seen that in Comparative Example 4, in which a commercially available touch fastener was used as a fixing member, adhesion of foreign substances to the fixing member could not be suppressed.

From Table 2, it can be seen that in Comparative Examples 5-6, in which a fixing member with a shear stress at the time of self-attachment being less than the predetermined value was used, when such fixing members were joined together, lateral displacement of the fixing members could not be suppressed.

INDUSTRIAL APPLICABILITY

According to the present disclosure, it is possible to provide a fixing member in which adhesion of foreign substances to its surface is suppressed, and which hardly causes lateral displacement when such fixing members are attached together to form a joined state.

Further, according to the present disclosure, it is possible to provide a laminated body that comprises a fixing member in which adhesion of foreign substances to its surface is suppressed, and which hardly causes lateral displacement when such fixing members are attached together to form a joined state.

REFERENCE SIGNS LIST 10, 20, 30, 30', 40, 40' laminated body
11, 21, 31, 31', 41, 41' substrate
12a, 12b, 22a-22h, 32, 32', fixing member
42a-42d, 42a'-42d' fixing member
50 laminated body
51 fixing member
52 carton paper
53 sliding piece
54 load cell
60, 60' laminated body (cut-out piece)
61, 61' substrate
62, 62' fixing member

The invention claimed is:

1. A fixing member comprising a surface having a coefficient of kinetic friction of 1.50 or less, an arithmetic mean roughness Ra of 5.00 μm or less, and a shear stress at the time of self-attachment of 100.00 N or more, wherein
the fixing member is formed from a cured product of a resin composition comprising a resin, a curing agent capable of curing the resin, and a silicone-based surface modifier.

2. The fixing member according to claim 1, wherein a content of the silicone-based surface modifier in the resin composition is 0.05 parts by mass or more and 1.7 parts by mass or less per 100 parts by mass of the resin.

3. The fixing member according to claim 1, wherein the silicone-based surface modifier is a polydimethylsiloxane-based surface modifier.

4. The fixing member according to claim 1, having a surface tackiness of 1.60 N or less.

5. A laminated body comprising: a substrate; and the fixing members as recited in claim 1.

6. A laminated body comprising: a substrate; a first fixing member located on the substrate; and a second fixing member located on the substrate, wherein
the first and second fixing members are abuttable against each other,
surfaces of the first and second fixing members each have a coefficient of kinetic friction of 1.50 or less,
the surfaces of the first and second fixing members each have an arithmetic mean roughness Ra of 5.00 μm or less,
a shear stress generated when the first and second fixing members are attached together is 100.00 N or more, and
the first and second fixing members are each independently formed from a cured product of a resin composition comprising a resin, a curing agent capable of curing the resin, and a silicone-based surface modifier.

7. The laminated body according to claim 5, being a tourniquet.

8. The laminated body according to claim 6, being a tourniquet.

\* \* \* \* \*